United States Patent [19]

Newhall

[11] 4,040,813

[45] Aug. 9, 1977

[54] PLANT REGULATOR COMPOSITIONS BASED ON 2-HYDROXYCYCLOALKYL QUATERNARY AMMONIUM COMPOUNDS

[75] Inventor: William F. Newhall, Winter Haven, Fla.

[73] Assignee: FMC Corporation, Philadelphia, Pa.

[21] Appl. No.: 555,952

[22] Filed: Mar. 6, 1975

Related U.S. Application Data

[63] Continuation-in-part of Ser. No. 319,126, Dec. 29, 1972, abandoned.

[51] Int. Cl.$^2$ .................... A01N 9/24; C07C 87/36
[52] U.S. Cl. .................................. 71/121; 71/70; 71/76; 71/86; 71/107; 260/501.15; 260/567.6 M
[58] Field of Search ............... 71/76, 121, 106, 107; 260/567.6 M

[56] References Cited

U.S. PATENT DOCUMENTS

| | | | |
|---|---|---|---|
| 3,482,961 | 12/1969 | Nickell et al. | 71/121 |
| 3,564,046 | 2/1971 | Newhall | 71/76 |
| 3,736,121 | 5/1973 | Zeeh et al. | 71/76 |

OTHER PUBLICATIONS

Robinson et al., "Absolute Configuration of Trans, etc.;" (1970) CA72 NO. 99889t. (1970).
Adank et al., "Esters of Cis and Trans Dimethylamino, etc.;" (1959) CA53 pp. 21799-21800 (1959).

*Primary Examiner*—Glennon H. Hollrah
*Attorney, Agent, or Firm*—Harrison H. Young, Jr.; Henry R. Ertelt

[57] ABSTRACT

Novel compositions including alkyl(2-hydroxycycloalkyl)-dimethylammonium salts as an essential active ingredient provide a method of regulating development of plants without killing the plants. The synthesis of members of the class of active compounds is described, and the utility of representative compositions is exemplified.

21 Claims, No Drawings

PLANT REGULATOR COMPOSITIONS BASED ON 2-HYDROXYCYCLOALKYL QUATERNARY AMMONIUM COMPOUNDS

CROSS REFERENCE TO RELATED APPLICATIONS

This application is a continuation-in-part of copending application Ser. No. 319,126 filed Dec. 29, 1972, now abandoned, the entire disclosure of which is incorporated herein by reference.

This invention pertains to the general field of plant regulators and particularly to compositions which control and regulate plant growth by retarding or stimulating said growth. Plant regulators are defined in the U.S. Department of Agriculture publication *Interpretation Number 3 of the Regulations for the Enforcement of the Federal Insecticide, Fungicide, and Rodenticide Act* (Revision 1, November 1964) at Section 362 – 101(a)(11).

It has been known that quaternary ammonium compounds exhibit biological activity, and plant regulator activity has been reported for quaternary ammonium derivatives of limonene, for example in U.S. Pat. No. 3,564,046 of Newhall, and for trimethylammonium derivatives containing a terpenoid moiety by H. Aruta, H. Yagi, T. Iwata and S. Tamura in Agr. Biol. Chem., 36, No. 5, 881–884 (1972). The unusual plant responses, such as the high order of plant regulator activity, caused by the 2-hydroxycyclohexylammonium compounds described herein, have not been previously suggested or reported.

This invention pertains to novel compositions for regulation of plant growth, comprising as an essential active ingredient either an alkyl(2-hydroxycycloalkyl)-dimethylammonium salt in which the alkyl group is C$_6$ to C$_{16}$, or a corresponding 2-ester, such as a compound having a 2-alkanoate group in place of the 2-hydroxy. These compositions are highly effective plant regulators, causing substantial growth retardation, growth stimulation, abscission of leaves and growing tips, and other growth anomalies on various species of plants, without causing death of the plants; they provide a method of regulating the development of plants without killing the plants.

The active compounds of the invention may be applied to deciduous trees, especially to fruit trees. Application to citrus has resulted in early maturation of fruit and enhanced marketability of fruit.

The invention also pertains to certain quaternary ammonium salts which are new compounds and which are effective in the regulation of plant growth. The invention also pertains to the enhancement of the activity of the compositions, particularly in terms of stimulatory effects, by certain specific spreader-activator adjuvants.

The active compounds of this invention are members of the class having the general formula:

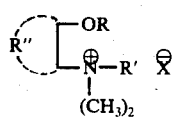

wherein R is H, lower alkanoyl, benzoyl, substituted lower alkanoyl, substituted benzoyl; R' is a straight or branched, saturated or unsaturated aliphatic radical of 6 – 16 carbon atoms; R'' is a saturated or unsaturated aliphatic diradical of 3 – 6 carbon atoms forming a 5- to 8-carbon ring with the 1,2-carbon atoms; and $\overset{\ominus}{X}$ is any agriculturally acceptable anion not of itself phytotoxic, the nature of which is not critical, as for example halide, sulfate, phosphate, sulfonate, and alkanoate of 1 – 8 carbon atoms.

Preferred compounds are those in which R is H, R' is a straight-chain hydrocarbon radical of 6 – 16 carbon atoms, and R'' is tetramethylene radical, which with the 1- and 2-carbon atoms forms a cyclohexane ring.

Particularly favorable plant regulator response to the active compounds has been noted with citrus fruits. Unlike apples, pears, or bananas, citrus fruits contain little or no starch and will not ripen after they are harvested. Thus quality as reflected in favorable changes in juice content, sugars, acidity, flavor and aroma must be obtained while the fruit is still on the tree. Minimum quality standards and official test methods have been set up by state bodies in citrus-growing states and adopted by the United States Department of Agriculture. Significant indicia of maturity and quality are juice content, total soluble solids (measured with a Brix hydrometer), acidity, and the ratio of Brix to total acid. These tests not only indicate whether the fruit meets minimum legal standarss for processing or shipping, but provide a basis on which the grower sells his fruit to the processor and on which the processor buys the fruit.

The preferred compounds may be prepared by the following sequence of reactions:

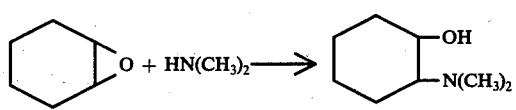

I

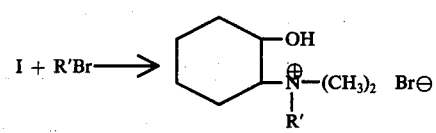

II

The acetates may be prepared by acylation of the quaternary salt:

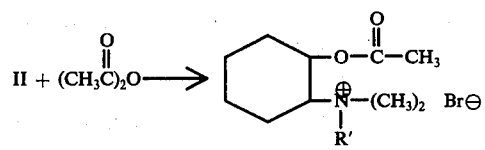

or by acylation of the amine, followed by quaternization:

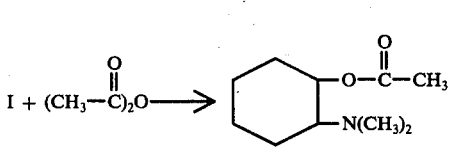

III

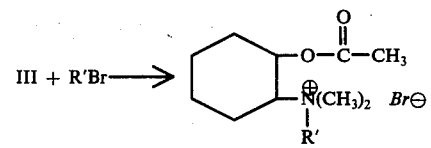

Synthesis of representative compounds is exemplified in the following examples. In the examples, all temperatures are in degrees centigrade, and all parts are by weight unless otherwise stated.

EXAMPLE 1

(2-Hydroxycyclohexyl)(dimethyl)octylammonium bromide a. 2-Dimethylamino-1-cyclohexanol A mixture of 50.0 g of cyclohexene oxide and 100 ml of 25 percent aqueous dimethylamine was heated with stirring at 145° in a small autoclave for 8 hours. While the mixture was being concentrated to dryness at 50° on a film evaporator, absolute ethanol was added periodically to aid in removal of water. The residue was distilled through a Nester-Faust spinning band column to give 53.0 g of 2-dimethylamino-1-cyclohexanol, b.p. 64.1 – 64.2/2.4 mm. The ir curve was consistent with the assigned structure.

b. (2-Hydroxycyclohexyl)(dimethyl)octylammonium bromide

A solution comprising 5 g of 2-dimethylamino-1-cyclohexanol, 10 g of 1-bromooctane and 5 ml of dimethylformamide was heated in a glass pressure bottle at about 95° for 16 hours. p-Xylene (25 ml) was added and the solution was concentrated at 60° using a film evaporator to remove dimethylformamide as its azeotrope with xylene. A second 25 ml portion of p-xylene was added and the azeotrope distilled until the residue was free of volatile material. This residue was dissolved in water, and the aqueous solution was extracted five times with diethyl ether. The aqueous solution was then concentrated under reduced pressure to give (2-hydroxycyclohexyl)(dimethyl)octylammonium bromide, a clear amorphous gum.

Analysis: Calc'd for $C_{16}H_{34}BrNO$: N 4.16 Found: N 4.23.

The quaternary salts in Examples 2 – 11 were prepared in the same manner, using the appropriate alkyl bromide.

EXAMPLE 2

Decyl(2-hydroxycyclohexyl)dimethylammonium bromide

Hygroscopic crystals.

Analysis: Calc'd for $C_{18}H_{38}BrNO$: N 3.84 Found: N 3.78.

EXAMPLE 3

Dodecyl(2-hydroxycyclohexyl)dimethylammonium bromide

Heavy colorless gum.

Analysis: Calc'd for $C_{20}H_{42}BrNO$: N 3.56 Found: N 3.64.

EXAMPLE 4

(2-Hydroxycyclohexyl)(dimethyl)tetradecylammonium bromide

Crystals from acetone; m.p. 89°–92°.

Analysis: Calc'd for $C_{22}H_{46}BrNO$: N 3.33 Found: N 3.38.

EXAMPLE 5

Hexadecyl(2-hydroxycyclohexyl)dimethylammonium bromide

Crystals from acetone; m.p. 97°–100°.

Analysis: Calc'd for $C_{24}H_{50}BrNO$: N 3.12 Found: N 3.20.

EXAMPLE 6

(2-Hydroxycyclohexyl)(dimethyl)nonylammonium bromide

Amorphous gum.

EXAMPLE 7

(2-Hydroxycyclohexyl)(dimethyl)undecylammonium bromide

Clear amber gum.

EXAMPLE 8

(2-Hydroxycyclohexyl)(dimethyl)tridecylammonium bromide

Deliquescent solid

EXAMPLE 9

(2-Hydroxycyclohexyl)(dimethyl)pentadecylammonium bromide

M.p. 65°–72°.

EXAMPLE 10

3-Hexyl(2-hydroxycyclohexyl)dimethylammonium bromide

Amorphous gum.

EXAMPLE 11

Heptyl(2-hydroxycyclohexyl)dimethylammonium bromide

Amorphous gum.

EXAMPLE 12

(2-Acetoxycyclohexyl)(dimethyl)dodecylammonium bromide

A mixture of 1.0 g of dodecyl(2-hydroxycyclohexyl)dimethylammonium bromide prepared in Example 3, 5 ml of acetic anhydride and 5 ml of dry pyridine was allowed to stand at room temperature for about 16 hours. Twenty-five milliliters of water was added and the mixture allowed to stand for one hour. The solution was concentrated under reduced pressure at 50° using a rotary film evaporator. Two 20 ml portions of water were added successively to aid removal of pyridine, followed by absolute ethanol for final drying. The residue was 1.11 g of (2-acetoxycyclohexyl)(dimethyl)dodecylammonium bromide. The ir spectrum was consistent with the assigned structure and clearly showed esterification of the hydroxy group to have occurred.

EXAMPLE 13

Cucumber Radicle Growth Retardation

Ten seeds of cucumber (*Cucumis sativus* L. var. Marketer) were placed on a piece of filter paper contained in a 9 cm Petri dish on which had been placed previously 4 ml of an aqueous solution of the compound at concentrations ranging from $2 \times 10^{-5}$ to $5 \times 10^{-4}$ molar. The filter paper was kept just sufficiently moist to avoid drying out of the seedlings. The Petri dishes were stored in the dark at 22°-24°. After 3 days, the length of the radicles was recorded and compared with a set of seeds which were untreated. The results summarized in Table I show that growth was retarded 80% or more by 10 of the 11 compounds when applied at a $5 \times 10^{-4}$ molar level, and by 6 of the 11 compounds when applied at a $2 \times 10^{-4}$ molar level.

Table I

| Cucumber Radicle Growth Retardation | | | |
|---|---|---|---|
| Compound of Example | Concentration, molar | Total Growth, mm. (sum of 3 replicates) | % Difference in Total Growth |
| 1 | $5 \times 10^{-4}$ | 68 | −87.3 |
|   | $2 \times 10^{-4}$ | 315 | −41.2 |
|   | $1 \times 10^{-4}$ | 417 | −22.2 |
|   | $5 \times 10^{-5}$ | 533 | − 0.5 |
|   | $2 \times 10^{-5}$ | 505 | − 0.7 |
|   | Untreated | 555 | — |
| 2 | $5 \times 10^{-4}$ | 60 | −88.8 |
|   | $2 \times 10^{-4}$ | 89 | −83.4 |
|   | $1 \times 10^{-4}$ | 138 | −74.3 |
|   | $5 \times 10^{-5}$ | 282 | −47.4 |
|   | $2 \times 10^{-5}$ | 401 | −25.2 |
|   | Untreated | 516 | — |
| 3* | $5 \times 10^{-4}$ | 58 | −90.8 |
|   | $2 \times 10^{-4}$ | 69 | −89.0 |
|   | $1 \times 10^{-4}$ | 173 | −72.5 |
|   | $5 \times 10^{-5}$ | 313 | −50.2 |
|   | $2 \times 10^{-5}$ | 596 | − 5.2 |
|   | Untreated | 629 | — |
| 4* | $5 \times 10^{-4}$ | 60 | −89.4 |
|   | $2 \times 10^{-4}$ | 115 | −79.6 |
|   | $1 \times 10^{-4}$ | 257 | −54.4 |
|   | $5 \times 10^{-5}$ | 511 | − 9.4 |
|   | $2 \times 10^{-5}$ | 633 | +12.2 |
|   | Untreated | 564 | — |
| 5* | $5 \times 10^{-4}$ | 172 | −80.0 |
|   | $2 \times 10^{-4}$ | 420 | −51.1 |
|   | $1 \times 10^{-4}$ | 591 | −31.2 |
|   | $5 \times 10^{-5}$ | 755 | −12.1 |
|   | $2 \times 10^{-5}$ | 818 | − 4.8 |
|   | Untreated | 859 | — |
| 6* | $5 \times 10^{-4}$ | 54 | −96.4 |
|   | $2 \times 10^{-4}$ | 164 | −89.7 |
|   | $1 \times 10^{-4}$ | 356 | −76.2 |
|   | $5 \times 10^{-5}$ | 533 | −64.2 |
|   | $2 \times 10^{-5}$ | 984 | −34.1 |
|   | Untreated | 1498 | — |
| 7* | $5 \times 10^{-4}$ | 58 | −96.5 |
|   | $2 \times 10^{-4}$ | 60 | −96.4 |
|   | $1 \times 10^{-4}$ | 170 | −89.9 |
|   | $5 \times 10^{-5}$ | 453 | −73.0 |
|   | $2 \times 10^{-5}$ | 726 | −56.8 |
|   | Untreated | 1680 | — |
| 8* | $5 \times 10^{-4}$ | 58 | −94.6 |
|   | $2 \times 10^{-4}$ | 77 | −92.8 |
|   | $1 \times 10^{-4}$ | 166 | −84.4 |
|   | $5 \times 10^{-5}$ | 296 | −72.2 |
|   | $2 \times 10^{-5}$ | 779 | −26.9 |
|   | Untreated | 1066 | — |
| 10* | $5 \times 10^{-4}$ | 104 | −89.1 |
|   | $2 \times 10^{-4}$ | 393 | −58.6 |
|   | $1 \times 10^{-4}$ | 556 | −41.5 |
|   | $5 \times 10^{-5}$ | 711 | −25.2 |
|   | $2 \times 10^{-5}$ | 939 | − 1.2 |
|   | Untreated | 950 | — |
| 11* | $5 \times 10^{-4}$ | 349 | −66.2 |
|   | $2 \times 10^{-4}$ | 662 | −35.9 |
|   | $1 \times 10^{-4}$ | 773 | −25.2 |
|   | $5 \times 10^{-5}$ | 977 | − 5.4 |
|   | $2 \times 10^{-5}$ | 1102 | + 6.7 |
|   | Untreated | 1033 | — |
| 12* | $5 \times 10^{-4}$ | 56 | −92.8 |
|   | $2 \times 10^{-4}$ | 60 | −92.3 |
|   | $1 \times 10^{-4}$ | 169 | −78.3 |
|   | $5 \times 10^{-5}$ | 419 | −46.3 |
|   | $2 \times 10^{-5}$ | 668 | −14.4 |
|   | Untreated | 780 | — |

*Read after 4 days

EXAMPLE 14

Alfalfa Seed Growth Retardation

One hundred seeds of alfalfa (*Medicago sativa* L. var. Hairy Peruvian) were placed in a Petri dish on filter paper wet with 2 ml of an aqueous solution of the test compound at concentrations ranging from $2 \times 10^{-4}$ to $5 \times 10^{-3}$ molar. After 48 hours in light, the seedlings were pressed gently between dry filter papers and then were weighed. Retardation was calculated as percent reduction in weight compared to weight of untreated seedlings and results are summarized in Table II. At a treatment level of $5 \times 10^{-3}$ molar, the compounds retarded seed growth by 32.6% to 45.9%.

Table II

| Alfalfa Seed Growth Retardation | | | |
|---|---|---|---|
| Compound of Example | Concentration, molar | Fresh Weight, g. (average of 3 replicates) | % Difference in Weight |
| 1 | $5 \times 10^{-3}$ | 0.6694 | −37.1 |
|   | $2 \times 10^{-3}$ | 0.7220 | −32.2 |
|   | $1 \times 10^{-3}$ | 0.7988 | −25.0 |
|   | $5 \times 10^{-4}$ | 0.8980 | −15.7 |
|   | $2 \times 10^{-4}$ | 0.9930 | − 6.7 |
|   | Untreated | 1.0648 | — |
| 2 | $5 \times 10^{-3}$ | 0.6491 | −37.6 |
|   | $2 \times 10^{-3}$ | 0.7025 | −32.5 |
|   | $2 \times 10^{-3}$ | 0.7855 | −24.5 |
|   | $5 \times 10^{-4}$ | 0.8808 | −15.4 |
|   | $2 \times 10^{-4}$ | 1.0177 | − 2.2 |
|   | Untreated | 1.0410 | — |
| 3 | $5 \times 10^{-3}$ | 0.6494 | −45.9 |
|   | $2 \times 10^{-3}$ | 0.7481 | −37.7 |
|   | $1 \times 10^{-3}$ | 0.8579 | −28.6 |
|   | $5 \times 10^{-4}$ | 1.0048 | −16.3 |
|   | $2 \times 10^{-4}$ | 1.1050 | − 8.0 |
|   | Untreated | 1.2010 | — |
| 4 | $5 \times 10^{-3}$ | 0.6848 | −34.1 |
|   | $2 \times 10^{-3}$ | 0.8798 | −15.3 |
|   | $1 \times 10^{-3}$ | 0.9501 | − 8.5 |
|   | $5 \times 10^{-4}$ | 1.0479 | + 0.9 |
|   | $2 \times 10^{-4}$ | 1.0748 | + 3.5 |
|   | Untreated | 1.0385 | — |
| 5 | $5 \times 10^{-3}$ | 0.7613 | −35.4 |
|   | $2 \times 10^{-3}$ | 0.9621 | −18.4 |
|   | $1 \times 10^{-3}$ | 1.0774 | − 8.6 |
|   | $5 \times 10^{-4}$ | 1.1821 | + 0.3 |
|   | $2 \times 10^{-4}$ | 1.1813 | + 0.2 |
|   | Untreated | 1.1790 | — |
| 6 | $5 \times 10^{-3}$ | 0.6447 | −39.9 |
|   | $2 \times 10^{-3}$ | 0.6892 | −35.8 |
|   | $1 \times 10^{-3}$ | 0.7726 | −28.0 |
|   | $5 \times 10^{-4}$ | 0.9019 | −15.9 |
|   | $2 \times 10^{-4}$ | 0.9896 | − 7.8 |
|   | Untreated | 1.0730 | — |
| 7 | $5 \times 10^{-3}$ | 0.6028 | −43.7 |
|   | $2 \times 10^{-3}$ | 0.6865 | −35.9 |
|   | $1 \times 10^{-3}$ | 0.8369 | −21.9 |
|   | $5 \times 10^{-4}$ | 0.9333 | −12.9 |
|   | $2 \times 10^{-4}$ | 1.0793 | + 0.8 |
|   | Untreated | 1.0712 | — |
| 8 | $5 \times 10^{-3}$ | 0.6611 | −35.4 |
|   | $2 \times 10^{-3}$ | 0.7749 | −24.3 |
|   | $1 \times 10^{-3}$ | 0.8221 | −19.7 |
|   | $5 \times 10^{-4}$ | 0.9538 | − 6.8 |
|   | $2 \times 10^{-4}$ | 0.9732 | − 4.9 |
|   | Untreated | 1.0238 | — |
| 10 | $5 \times 10^{-3}$ | 0.6626 | −38.0 |
|   | $2 \times 10^{-3}$ | 0.7316 | −32.7 |
|   | $1 \times 10^{-3}$ | 0.8148 | −25.0 |
|   | $5 \times 10^{-4}$ | 0.9933 | − 8.6 |
|   | $2 \times 10^{-4}$ | 1.0469 | − 3.7 |
|   | Untreated | 1.0868 | — |
| 11 | $5 \times 10^{-3}$ | 0.7232 | −32.6 |
|   | $2 \times 10^{-3}$ | 0.7546 | −29.7 |
|   | $1 \times 10^{-3}$ | 0.8426 | −21.5 |
|   | $5 \times 10^{-4}$ | 0.9813 | − 8.6 |
|   | $2 \times 10^{-4}$ | 1.0190 | − 5.1 |
|   | Untreated | 1.0737 | — |

EXAMPLE 15

Grapefruit Seed Growth Retardation by Seed Soak Method

For each treatment, both the outer and inner seed coats were removed from 10 mature grapefruit seeds. The peeled seeds were soaked for 16 hours in an aqueous solution containing the test compound at a specified concentration. The seeds were then planted in No. 10 metal cans lined with plastic bags and containing a 1:1 mixture of sand and expanded mica. The cans were covered with glass plates so as to retain a high humidity while the plants emerged. Thirty days after planting the seeds, the plants were harvested and the fresh weights of lateral roots, taproot and plant top were determined. These values are summarized in Table III. Root weights and plant top weights were substantially reduced by treatment with a $1 \times 10^{-3}$ molar solution of decyl(2-hydroxycyclohexyl)dimethylammonium bromide.

Table III

Grapefruit Seed Growth Retardation by Seed Growth Method Using Compound of Example 2

| Concentration, molar | Laterals Weight | % Reduction | Taproot Weight | % Reduction | Tops Weight | % Reduction |
|---|---|---|---|---|---|---|
| $1 \times 10^{-3}$ | 0.108 | 80.8 | 0.898 | 43.6 | 1.773 | 44.7 |
| $5 \times 10^{-4}$ | 0.399 | 29.0 | 1.293 | 18.7 | 1.498 | 53.3 |
| $2 \times 10^{-4}$ | 0.456 | 18.9 | 1.421 | 10.7 | 3.031 | 5.5 |
| $1 \times 10^{-4}$ | 0.429 | 23.7 | 1.478 | 7.1 | 2.907 | 9.4 |
| Untreated | 0.562 | — | 1.591 | — | 3.209 | — |

EXAMPLE 16

Grapefruit Seed Growth Retardation by Radicle Growth Method

Ten peeled grapefruit seeds were placed on filter paper which was moistened by addition thereto of 4 ml of an aqueous solution of the test compound at a specific concentration. The germinating seeds were maintained in the dark at room temperature for 14 days during which period 2 ml of water was added to each dish on each of two occasions to prevent the seedlings from drying out. At the end of 14 days, the radicles were measured. The results summarized in Table IV show substantial growth retardation, 70% or greater for each compound at a $1 \times 10^{-3}$ molar level.

TABLE IV

Grapefruit Radicle Growth Retardation

| Compound of Example | Concentration, molar | Total Growth, mm | % Difference from Untreated |
|---|---|---|---|
| 1 | $2 \times 10^{-3}$ | 52 | −94.5 |
|   | $1 \times 10^{-3}$ | 231 | −75.6 |
|   | $5 \times 10^{-4}$ | 693 | −26.6 |
|   | $2 \times 10^{-4}$ | 1235 | +31.5 |
|   | Untreated | 939 | — |
| 2 | $2 \times 10^{-3}$ | 17 | −98.0 |
|   | $1 \times 10^{-3}$ | 109 | −87.7 |
|   | $5 \times 10^{-4}$ | 241 | −72.8 |
|   | $2 \times 10^{-4}$ | 665 | −24.9 |
|   | Untreated | 885 | — |
| 3 | $4 \times 10^{-4}$ | 148 | −79.7 |
|   | $2 \times 10^{-4}$ | 289 | −60.4 |
|   | $1 \times 10^{-4}$ | 433 | −40.6 |
|   | Untreated | 729 | — |
| 4 | $2 \times 10^{-3}$ | 68 | −88.6 |
|   | $1 \times 10^{-3}$ | 92 | −84.6 |
|   | $5 \times 10^{-4}$ | 152 | −74.5 |
|   | $2 \times 10^{-4}$ | 277 | −53.5 |
|   | Untreated | 596 | — |
| 5 | $2 \times 10^{-3}$ | 109 | −83.8 |
|   | $1 \times 10^{-3}$ | 200 | −70.3 |
|   | $5 \times 10^{-4}$ | 258 | −61.7 |
|   | $2 \times 10^{-4}$ | 453 | −32.8 |
|   | Untreated | 674 | — |

EXAMPLE 17

Grapefruit Seedling Growth Retardation

Forty grapefruit seedlings selected from uniformity of growth were cut back to a uniform 25 cm from the top of the container in which they were growing. Each seedling was treated by spraying thereon exactly 15 ml of an aqueous solution of the compound of Example 2 at a specified concentration. Ten seedlings were treated with each concentration. A cover had been placed over the soil to prevent dripping of the solution onto the soil and subsequent uptake by the plant root system. New growth was measured after 2 weeks and again after 3 weeks to determine growth retardation. At the end of the fourth week, all new growth was cut from the seedlings and weighed. All plants were then cut back to a uniform 6 inches. After 4 more weeks, new growth was again trimmed off and weighed. Results are summarized in Table V.

Table V

Grapefruit Seedling Growth Retardation Ten Plants per Treatment

| | Treatment ppm of Compound of Example 2 | | | |
|---|---|---|---|---|
| | 1000 | 2000 | 3000 | Untreated |
| Total number of shoots | | | | |
| 15 days | 19 | 31 | 16 | 29 |
| 21 days | * | ** | 19 | 29 |
| Average growth per shoot, mm | | | | |
| 15 days | 31.1 | 43.5 | 18.4 | 49.1 |
| 21 days | * | ** | 99.0 | 140.4 |
| Difference from control, % | | | | |
| 15 days | −36.7 | −11.4 | −62.3 | — |
| 21 days | * | ** | −29.5 | — |
| New growth, g | | | | |
| 0–28 days | 96.5 | 110.6 | 87.2 | 129.1 |
| 28–56 days | 65.1 | 53.2 | 77.4 | 69.0 |
| 0–56 days | 161.6 | 163.8 | 164.6 | 198.1 |
| Difference from control, % | | | | |
| 0–28 days | −25.3 | −14.3 | −32.5 | — |
| 28–56 days | − 5.7 | −22.9 | +12.2 | — |
| 0–56 days | −18.4 | −17.3 | −16.9 | — |

*Resembled untreated seedlings; not measured.
**Growth appeared stimulated; not measured.

Within each 10-plant group, considerable variation in growth retardation was observed. The group treated at 2000 ppm appears anomalous at the 15-day reading owing to the contribution of two plants. These two plants produced 11 shoots averaging 83 mm per shoot. (From this it is seen that the other 20 shoots thus averaged approximately 20 mm per shoot).

EXAMPLE 18

Grapefruit Seedling Growth Retardation

Sixty grapefruit seedlings were pruned to a height of 25 cm, and after new growth had developed (22 days), foliar sprays were applied to the point of run-off. Each of 10 seedlings was treated by spraying with 20 ml of an aqueous solution containing 3000 ppm of a test compound and 1% of Regulaid polyoxyethylene polypropoxypropanol, a nonionic spreader-activator. A soil cover was used to prevent spray droplets from contacting the soil. The increase in height of the plants was measured at weekly intervals and the results are summarized in Table VI, showing retardation or acceleration in growth relative to controls sprayed with a 1% Regulaid solution.

Table VI

Growth Response of Grapefruit Seedlings to 3000 ppm of Compound (+ 1% Regulaid)*

% Retardation (−) or % Acceleration (+) Compared to Untreated

| Period | Ex. 1 | Ex. 2 | Ex. 3 | Ex. 4 | Ex. 5 |
| --- | --- | --- | --- | --- | --- |
| 1 week | − 6 | −69 | −82 | −36 | −38 |
| 2 week | −15 | −76 | −94 | −42 | −40 |
| 3 week | −16 | −76 | −95 | −40 | −40 |
| 4 week | − 8 | −59 | −59 | −22 | − 9 |
| 5 week | 0 | −53 | 0 | 0 | 0 |
| 6 week | − 6 | −32 | +98 | +52 | +39 |
| 7 week | −19 | + 8 | +102 | +54 | +43 |
| 8 week | −16 | +61 | +98 | +48 | +52 |
| 9 week | + 5 | +66 | +72 | +39 | +49 |
| 10 week | +16 | +20 | +19 | +12 | +19 |

*Average response of 10 plants per treatment.

Observations of these seedlings 1 week after application of the spray indicated that phytotoxicity increased with the length of the alkyl group on the quaternary compound. Seedlings treated with the compounds of Example 1 having an 8-carbon alkyl group showed essentially no effects of phytotoxicity, with only slight leaf curl at point of spray application, but new growth normal. The compound of Example 2 with a 10-carbon chain also caused leaf curl at the point of spray application, and necrosis and some new leaf abscission. The compound of Example 3, having a 12-carbon chain, produced a general abscission of tiny new leaves, but of no older leaves, and all 10 seedlings abscissed their growing tips; this was a true abscission and not dieback, since the tips abscissed were green at the base and the pedestals from which they abscissed were also green. The compounds of Example 4 ($C_{14}$) and Example 5 ($C_{16}$) caused abscission and abnormal growth and severe leaf damage, the $C_{16}$ compound the more damaging.

It is seen in Table VI that retardation declined after the third week and an acceleration of growth relative to the growth of untreated seedlings began to manifest itself in the sixth week. The original inhibition was overcome and growth was stimulated. Two of the compounds (Examples 2 and 3) were also treated at 2,000 ppm and 4,000 ppm levels, with results summarized in Table VII.

Table VII

Growth Response of Grapefruit Seedlings to 2000 ppm and 4000 ppm of Compound (+ 1% Regulaid)

| | Example 2 | | Example 3 | |
| --- | --- | --- | --- | --- |
| Period | 2000 ppm | 4000 ppm | 2000 ppm | 4000 ppm |
| 1 week | −33 | −45 | −33 | −88 |
| 2 week | −34 | −45 | −33 | −89* |
| 3 week | −36 | −40 | −21 | −95 |
| 4 week | −22 | − 9 | +16 | −66 |
| 5 week | + 9 | +30 | +65 | −43 |
| 6 week | +19 | +26 | +56 | −39 |
| 7 week | − 4 | − 8 | +21 | −51 |
| 8 week | 0 | −11 | +20 | −50 |
| 9 week | −18 | −26 | + 5 | −56 |
| 10 week | −23 | −31 | − 2 | −56 |

*All 10 plants experienced apical abscission.

EXAMPLE 19

Black Valentine Bean Growth Retardation

Individually potted, rapidly growing young (8 days old) Black Valentine bean plants were sprayed to runoff with aqueous solutions containing the compound of Example 2 at specified concentrations. Ten plants were treated at each concentration. Measurements were made of the length of the second internode and of total plant height 7 days after treatment. Results summarized in Table VIII show internodal height to be severely shortened, and total plant height substantially reduced.

Table VIII

Black Valentine Bean Growth Retardation with Compound of Example 2

| Concentration, ppm | Internodal Height | | Total Plant Height | |
| --- | --- | --- | --- | --- |
| | mm | % Difference | mm | % Difference |
| 3000 | 7.8 | −92.2 | 149.0 | −60.5 |
| 2000 | 8.8 | −91.1 | 173.5 | −54.0 |
| 1000 | 11.3 | −88.7 | 176.8 | −53.2 |
| Untreated | 99.7 | | 377.4 | |

A similar study using the compound of Example 4 on five plants per replicate is summarized in Table IX. Retardation comparable to that obtained with the compound of Example 2 was obtained at lower levels of treatment with the compound of Example 4.

Table IX

Black Valentine Bean Growth Retardation with Compound of Example 4

| Concentration ppm | Length of Second Internode | | Total Plant Height | | Primary Leaf Diameter | |
| --- | --- | --- | --- | --- | --- | --- |
| | mm | % Difference | mm | % Difference | mm | % Difference |
| 1000 | 7.0 | −93.9 | 110.6 | −62.9 | 71.8 | −10.4 |
| 500 | 12.8 | −88.8 | 144.2 | −51.7 | 84.3 | + 5.9 |
| 250 | 14.6 | −87.2 | 131.4 | −56.0 | 81.4 | + 2.3 |
| 125 | 23.0 | −79.9 | 143.4 | −60.0 | 77.5 | − 2.7 |
| 62 | 72.0 | −37.0 | 242.2 | −18.9 | 87.4 | +10.2 |
| 31 | 91.8 | −19.7 | 263.6 | −11.7 | 89.2 | +12.1 |
| Untreated | 114.3 | | 298.5 | | 79.6 | |

EXAMPLE 20

Growth Response to Black Valentine Bean Plants

Test compounds at a concentration of 1% in lanolin containing 2.5% of Tween 80 polyoxyethylene sorbitan monooleate were applied to Black Valentine bean plants. A 15- to 20-mg ring of these pastes was applied to the first internode of plants when the primary leaves were fully expanded and the trifoliate leaves were still tightly folded in the terminal buds (plants approximately 7 days old). The length of the second internode was measured after 7 days' further growth in the greenhouse. Each compound was run on six bean plants, and there were six lanolin-treated controls; the test series was run three times. The average percent reduction in growth of the second internode, as compared with the average for the controls, is recorded in Table X. Test results recorded in U. S. Pat. No. 3,564,046, obtained when alkyl dimethyl(1-hydroxy-p-menth-2-yl)ammonium bromides (the "limonene derivatives") were applied to 7-day-old Black Valentine bean plants at a concentration of 1% in lanolin containing 2.5% of Tween 80 surfactant, are recorded in Table X for comparison. Three of the cyclohexanol quaternary compounds (heptyl, octyl, and nonyl) produce significantly more growth retardation than the most effective of the "limonene derivatives" (heptyl), and the decyl cyclohexanol compound is just as effective as the heptyl limonene derivative. It is surprising to find simpler, easily synthesized molecules (the cyclohexanol derivatives) showing greater activity than the structurally more complex derivatives of a natural product (the limonene derivatives).

Table X
Growth Response of Black Valentine Bean Plants
Percent Growth Reduction in Second Internode Compared with Untreated Plants

| Alkyl Group | Cyclohexanol Quaternaries Example No. | % | Limonene Quaternaries (U.S.3,564,046) % |
|---|---|---|---|
| Ethyl | | | 21 |
| Propyl | | | 30 |
| Butyl | | | 50 |
| Pentyl | | | 62 |
| Hexyl | | | 77 |
| Heptyl | 11 | 83.5 | 80 |
| Octyl | 1 | 88.4 | 70 |
| Nonyl | 6 | 88.7 | 49 |
| Decyl | 2 | 79.8 | 25 |
| Undecyl | 7 | 73.5 | |
| Dodecyl | 3 | 54.8 | 17 |
| Tridecyl | 8 | 56.9 | |
| Tetradecyl | 4 | 43.5 | |
| Pentadecyl | 9 | 38.4 | |
| Hexadecyl | 5 | 31.2 | |
| Octadecyl | | | 5 |

EXAMPLE 21

Response of Mature Grapefruit Trees

Juices of citrus fruits contain a large number of soluble constituents, chiefly sugars, with smaller amounts of organic acids, vitamins, proteins, free amino acids, essential oils, glucosides and other compounds also present. Approximately 85% of the total soluble solids are sugars. They are measured as such in official tests by means of a Brix hydrometer. This instrument, which actually measures specific gravity, is calibrated to read directly in degrees Brix or percent pure sucrose at a temperature of 17.5° C. In citrus testing, the term Brix or degrees Brix is synonymous with total soluble solids and is not to be confused with "pounds-solids".

Acid in citrus juices is principally citric acid, with smaller amounts of malic, tartaric, and succinic acids also present. The "total-acid", properly termed "titratable acid", is found by titration with standard alkali, and it is calculated as anhydrous citric acid.

Proportion of Brix to total acid, or "ratio", plays a large part in palatability. Hence, when sugars are low, "ratio" requirements are increased so that acid is proportionately even lower. This makes the sugars more perceptible to the taster's palate. Maturity requirements for most varieties of citrus fruits include a minimum ratio which must be met regardless of the Brix content of the juice, however. For frozen concentrates, fruit of the highest possible internal quality is desired, since, in addition to having better flavor and aroma, values rise rapidly as the quantity of juice and Brix increases. Most processing plants buy their fruit for concentrate on the basis of pounds-solids. Pounds-solids are calculated by multiplying the weight of juice per standard box of fruit by the Brix divided by 100. The pounds-solids per box so obtained are then multiplied by the going price per pound of solids to obtain the price per box of fruit.

In this example, mature Marsh grapefruit trees at least 14 years old, and having borne fruit during the nine preceding seasons, were sprayed to run-off with an aqueous solution containing 2,000 ppm of the compound of Example 4 and 1% of Regulaid polyoxyethylene polyoxypropanol, a non-ionic spreader-activator. Nine trees were sprayed once in May, four trees were sprayed once in August, and three trees were sprayed twice, once in each of May and August. Spray equipment utilizing a high-pressure mist nozzle was employed, and approximately 10 gallons of solution was used for each of the trees sprayed. The temperature at the time of spraying was circa 80° F (26.7° C). There was light rainfall 2 days after spraying, both in May and August. The first spraying (in May) was within the period 6 to 8 weeks after first bloom, by which time blossoms have fallen and fruit set has occurred, so tiny fruit are just visible. The spraying in August, 11 weeks after the first spray, was made to determine whether later spraying or a second spraying would be beneficial.

To serve as controls, fruit was taken from ten trees not sprayed with active ingredient in the same grove of Marsh grapefruit trees.

In September, 17 weeks after the first spray application and 6 weeks after the second, 20 grapefruit were picked from trees sprayed in May only, 20 were picked from trees sprayed in August only, 20 were picked from trees sprayed both in May and in August, and 20 were picked from trees not sprayed. Selection of fruit for picking was made according to standard methods designed to insure that the samples were representative in each case.

On each of the four 20-grapefruit samples (May spraying, August spraying, May and August spraying, and untreated), determinations were made of juice content, Brix (total soluble solids) and total (titratable) acid, employing official methods of the Florida Citrus Code of 1949, as amended, Chapter 601, Florida Statutes. These official methods are incorporated in U. S. standards for grade under authority of the U. S. Secretary of Agriculture. These may be found at Title 7, Code of Federal Regulations — Agriculture, Chapter 1, Agriculture Marketing Service (standards, inspection, marketing practices), Department of Agriculture, part 52, processed fruits and vegetables, processed products thereof, and certain other processed food products.

A second picking was carried out in November, 6 weeks after the first, and a third picking was carried out in January, 8 weeks after the second. The same selection procedures were used in November and January as in September, and determinations of juice content, Brix and acidity were made on the fruit picked.

Results recorded in Table XI show that fruit from trees sprayed in May contained more juice, had higher Brix (therefore higher soluble solids, equated with sugar content), and had lower acidity than the untreated trees. Further, the ratio of Brix to acid was higher for trees treated in May than for the untreated controls.

Before grapefruit is considered sufficiently mature for processing or shipping, the Brix/acid ratio must be 7.0 for Brix below 9.1. As Brix increases from 9.1 to 10.1, the ratio requirement declines linearly from 7.0 to 6.5, and as Brix increases from 10.1 to 12.0, the ratio requirements declines linearly from 6.5 to 6.0. For higher levels of Brix, the ratio must be at least 6.0. Fruit which does not meet these levels is not marketable and ordinarily is not harvested. By inspection of the results recorded in Table XI, it is seen that the untreated fruit did not meet the required minima up to the time of the January picking, while fruit sprayed in May had already surpassed the 7.0 level by the time of the November picking 8 weeks earlier. Thus all of the fruit from trees sprayed in May could have been harvested sometime between September and November. The fruit sprayed in August fell short of the 7.0 level in November, but by January the Brix had increased sufficiently to make the 6.76 ratio acceptable. Fruit sprayed both in May and in August showed less improvement in ratio than was obtained from a single spraying in either May or August, and had not reached an acceptable ratio by January, though even it was slightly better than untreated fruit by that time.

Due to drouth conditions during October, November and December, the trees were withdrawing water from the fruit, and this is evidenced in the increase of acidity for fruit from untreated trees. In contrast, fruit from trees sprayed in May showed relatively little increase in acidity from September to January. Another effect of the drouth is seen in the decline in juice level between the November picking and the January picking. This was more pronounced for the untreated trees (16.3%) than for the trees sprayed in either May (10.7%) or August (10.1%). Juice content would be expected to continue to rise in all cases. The plant regulator both induces higher juice content and inhibits withdrawal of water from the fruit under drouth conditions.

small amount of wetting, dispersing, or emulsifying agent for facilitating dispersion. Typical wetting, dispersing, or emulsifying agents used in agricultural formulations include, for example, polyoxyethylene condensates; copolymers of polyoxyethylene and polyoxypropylene; polyhydric alcohols; and other types of surface-active agents compatible with quaternary ammonium salts, which, in formulations where they are used, normally comprise from 1% to 15% by weight of the formulation.

Resinous paste formulations are mixtures containing the active ingredient dispersed or suspended in an inert solid or semisolid organic substance obtained as an exudate of various plant or animal matter or prepared synthetically. Typical examples of resinous organic substances employed as carriers for the active ingredient include lanolin, asphalt, agar, and paraffin. These resinous paste formulations may contain between 0.01% and Table XI Response of Mature Marsh Grapefruit Trees
Sprayed to run-off with solution containing 2000 ppm of compound of Example 4; fruit sampled in September, November and January (17, 23 and 31 weeks after May spraying; 6, 12 and 20 weeks after August spraying)

|  | % Juice | | | Brix[1] | | | Acid[2] | | | Ratio Brix/Acid | | | Pounds-Solids[3] | | |
|---|---|---|---|---|---|---|---|---|---|---|---|---|---|---|---|
|  | Sept. | Nov. | Jan. | Sept. | Nov. | Jan. | Sept. | Nov. | Jan. | Sept. | Nov. | Jan. | Sept. | Nov. | Jan. |
| May spray | 50.6 | 51.2 | 45.7 | 8.3 | 9.1 | 10.1 | 1.26 | 1.23 | 1.35 | 6.59 | 7.40 | 7.48 | 4.19 | 4.66 | 4.61 |
| August spray | 45.4 | 50.7 | 45.6 | 8.0 | 8.4 | 9.8 | 1.22 | 1.21 | 1.45 | 6.54 | 6.94 | 6.76 | 3.62 | 4.26 | 4.47 |
| May & August spray | 42.9 | 49.8 | 40.8 | 8.0 | 8.2 | 10.6 | 1.33 | 1.23 | 1.72 | 5.98 | 6.67 | 6.16 | 3.41 | 4.08 | 4.32 |
| Untreated | 40.7 | 47.3 | 39.6 | 8.4 | 9.3 | 10.6 | 1.31 | 1.58 | 1.73 | 6.41 | 5.89 | 6.13 | 3.41 | 4.39 | 4.20 |

[1]Total soluble solids measured with a Brix hydrometer, calibrated to read in % pure sucrose
[2]Titratable acid calculated as % anhydrous citric acid
[3]Pounds-solids = pounds-solids per 100 pounds of fruit — % juice × Brix/100

For application to plants, these quaternary ammonium salts are normally not used undiluted, but are combined with any of a variety of adjuvants and carriers normally employed for facilitating the dispersion of active ingredients for agricultural applications, recognizing the fact that the formulation and mode of application of a toxicant may affect the activity of that toxicant in a given application. Thus, the quaternaries may be formulated as emulsifiable concentrates, as solutions, as wettable powders, as flowable pastes, as resinous pastes, or as any of several other known types of formulations, depending on the desired mode of application. For regulation of established plant growth, sprays are most commonly used. Formulations suitable for use in these applications may contain as little as a few parts per million or as much as 95% or more by weight of active ingredient.

Emulsifiable concentrates are homogeneous liquids which may be quite free-flowing or highly viscous, which are dispersible in water or other dispersant and which normally also contain a liquid carrier such as xylene, heavy aromatic naphthas, isophorone, and other nonvolatile organic solvents. Solvents are homogeneous compositions in which the active ingredient is soluble in the inert liquid carrier and the combination is soluble in the final dispersant.

Wettable powders are in the form of finely divided particles which disperse readily in water or other dispersant. The wettable powder is ultimately applied to the plant growth either as a dry powder or as an emulsion in water or other liquid. Typical carriers for wettable powders include fuller's earth, kaolin clays, silicas and other highly absorbent, readily wet inorganic diluents. Wettable powders are normally prepared to contain about 5-80% of active ingredient, depending on the absorbency of the carrier. They usually also contain a 50% of active ingredient. For application, these resinous paste formulations are applied to plants directly to the locus of desired application as the concentrated formulation or may first be diluted to a desired concentration of active ingredient by admixture with additional inert carrier substance.

Flowable paste formulations are mixtures of very finely divided active ingredients suspended in an emulsifying agent or other surface-active agent in the case of the highly concentrated flowable paste, or are suspensions in mixtures of water or other dispersing liquid with the emulsifying agent. These flowable paste concentrations may contain between 10% and 90% of active ingredient.

Other useful formulations include dusts which are admixtures of the active ingredient with finely divided solids such as talc, attapulgite clays, kieselguhr, and other organic and inorganic solids which act as dispersants and carriers for the toxicants; these finely divided solids have an average particle size of less than 50 microns in diameter.

For application, these concentrated formulations are usually dispersed in water or other liquid carrier and applied as a spray to the plant growth to be treated. Or, in the case of solid formulations, application is carried out by dusting the toxicant formulation onto the plant growth to be controlled at a time when the normal leaf surface is in a condition such that the dust particles will adhere to the leaf surface.

The quaternary ammonium salts of this invention may be combined with other active ingredients. For example, the compounds of this invention may be formulated and/or applied with insecticides, fungicides, nematicides, other plant regulators, fertilizers, and other agricultural chemicals. In applying these active compounds, formulated alone or with other agricultural chemicals,

I claim:
1. Plant regulator composition comprising
    a. as active ingredient an effective amount of a compound of the formula:

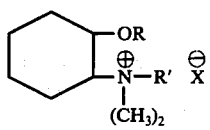

wherein R is H, alkanoyl of 2-3 carbon atoms, or benzoyl; R' is a straight or branched, saturated or unsaturated hydrocarbon radical of 6-16 carbon atoms; and $\overset{\ominus}{X}$ is an agriculturally acceptable, non-phytotoxic anion;
    b. an inert agricultural carrier; and
    c. a compatible surface-active agent.

2. The composition of claim 1 in which R is H, R' is a straight-chain hydrocarbon radical, of 6-16 carbon atoms, and X is chlorine, bromine, or iodine.

3. The composition of claim 2 in which R' is decyl radical and X is bromine.

4. The composition of claim 2 in which R' is undecyl radical and X is bromine.

5. The composition of claim 2 in which R' is dodecyl radical and X is bromine.

6. The composition of claim 2 in which R' is tetradecyl radical and X is bromine.

7. Method for regulation of plant growth which comprises applying to the plant wherein regulation is desired an effective amount of a compound of the formula:

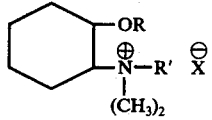

wherein R is H, alkanoyl of 2-3 carbon atoms, or benzoyl; R' is a straight or branched, saturated or unsaturated, hydrocarbon radical of 6-16 carbon atoms; and $\overset{\ominus}{X}$ is an agriculturally acceptable non-phytotoxic anion.

8. The method of claim 7 in which R is H, R' is a straight-chain hydrocarbon of 6-16 carbon atoms, and X is chlorine, bromine, or iodine.

9. The method of claim 8 in which R' is decyl radical and X is bromine.

10. The method of claim 8 in which R' is undecyl radical and X is bromine.

11. The method of claim 8 in which R' is dodecyl radical and X is bromine.

12. The method of claim 8 in which R' is tetradecyl radical and X is bromine.

13. Compound of the formula:

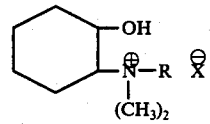

wherein R is a saturated hydrocarbon chain of 10-14 carbon atoms, and $\overset{\ominus}{X}$ is chloride, bromide, or iodide.

14. Compound of claim 13 which is decyl-(2-hydroxycyclohexyl)dimethylammonium bromide.

15. Compound of claim 13 which is (2-hydroxycyclohexyl)(dimethyl)undecylammonium bromide.

16. Compound of claim 13 which is dodecyl-(2-hydroxycyclohexyl)dimethylammonium bromide.

17. Compound of claim 13 which is (2-hydroxycyclohexyl)(dimethyl)tetradecylammonium bromide.

18. Method for accelerating the maturation of citrus fruit which comprises applying to the citrus trees an effective amount of a compound of the formula:

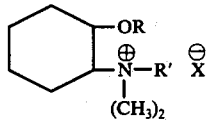

wherein R is H, alkanoyl of 2-3 carbon atoms, or benzoyl; R' is straight or branched, saturated or unsaturated, hydrocarbon radical of 6-16 carbon atoms; and $\overset{\ominus}{X}$ is an agriculturally acceptable non-phytotoxic anion.

19. The method of claim 18 in which R is H, R' is a straight-chain hydrocarbon radical of 6-16 carbon atoms, and X is chlorine, bromine, or iodine.

20. The method of claim 19 in which R' is 10-16 carbon atoms and X is chlorine or bromine.

21. The method of claim 19 in which the citrus trees are grapefruit trees, R' is tetradecyl radical, X is bromine, and the compound is applied after fruit set.

UNITED STATES PATENT AND TRADEMARK OFFICE
CERTIFICATE OF CORRECTION

PATENT NO. : 4,040,813
DATED : August 9, 1977
INVENTOR(S) : William F. Newhall

It is certified that error appears in the above-identified patent and that said Letters Patent are hereby corrected as shown below:

Abstract, line 2, "cloalkyl)-dimethylammonium" should read --cloalkyl)dimethylammonium--. Column 1, line 26, "36", should read --$\underline{36}$--. Column 3, line 28, "p-Xylene" should read --$\underline{p}$-Xylene--; line 31, "p-xylene" should read --$\underline{p}$-xylene--. Column 4, line 24, "solid" should read --solid.--. Column 5, line 13, "3 replicates" should read --3 replicates)--. Column 6, line 18, "2 X $10^{-3}$" should read --1 X $10^{-3}$--. Column 7, line 62, "from" should read --for--. Column 8, line 27, "Treatment" should read --Treatment,--. Column 10, line 36, "to" should read --of--. Column 12, line 54, "ments" should read --ment--.

Column 16, line 23, "decyl-(2-hydrox-" should read --decyl(2-hydrox- --; line 27, "dodecyl-(2-" should read --dodecyl(2- --.

Signed and Sealed this

Fifteenth Day of May 1979

[SEAL]

Attest:

RUTH C. MASON
Attesting Officer

DONALD W. BANNER
Commissioner of Patents and Trademarks